United States Patent [19]

Courtney et al.

[11] Patent Number: 5,650,301
[45] Date of Patent: Jul. 22, 1997

[54] HIRUDIN HV2 HAVING A SN7LYS SUBSTITUTION, METHOD OF MAKING, AND METHOD OF USE

[75] Inventors: Michael Courtney, Geudertheim; Eric DeGryse; Gérard Loison, both of Strasbourg; Yves LeMoine, Strasbourg-Neudorf, all of France

[73] Assignee: Transgene S.A., Courbevoie, France

[21] Appl. No.: 480,511

[22] Filed: Jun. 7, 1995

Related U.S. Application Data

[63] Continuation of Ser. No. 197,449, Feb. 16, 1994, abandoned, which is a continuation of Ser. No. 967,548, Oct. 27, 1992, abandoned, which is a continuation of Ser. No. 627,876, Dec. 13, 1990, abandoned, which is a continuation of Ser. No. 127,159, Dec. 1, 1987, abandoned.

[30] Foreign Application Priority Data

Dec. 1, 1986 [FR] France ................................. 86 16723

[51] Int. Cl.⁶ ................. C12P 21/06; C12N 15/00; C07K 14/815
[52] U.S. Cl. ................. 435/71.1; 435/69.1; 435/320.1; 435/243; 514/2; 530/300
[58] Field of Search ................. 530/300; 435/69.1, 435/21.1, 240.11, 320.1, 243; 514/2

[56] References Cited

FOREIGN PATENT DOCUMENTS

| | | |
|---|---|---|
| 158564 | 10/1985 | European Pat. Off. . |
| 168342 | 1/1986 | European Pat. Off. . |
| 171024 | 2/1986 | European Pat. Off. . |
| 200655 | 11/1986 | European Pat. Off. . |
| 8603517 | 6/1986 | WIPO . |

OTHER PUBLICATIONS

Rydel et al., Science, 1990, vol. 249, pp. 277–280.
Thrombin Inhibition by Hirudin Fragments: Possible Mechanism of Hirudin–Thrombin Interaction; S. Bajusz, I. Fauszt, E. Barabas, M. Dioszegi, et al.
Itakura et al. Science vol. 209 pp. 1401–1405 (1980).
Harvey, R.P. et al., "Cloning and expression of a DNA coding for the antiocoagulant hirudin from the bloodsucking leech, Hirudo medicinalis" From Report —Proceedings fo the National Academy of Sciences of the USA 83 (1986), pp. 1084–1088.
Harvey, R.P. et al., "Cloning and expresion of a cDNA coding for the anticoagulant hirudin from the bloodsucking leech, Hirudo medicinalis" From Report —Proceedings of the National Academy of Sciences of the USA 83 (1986), pp. 1084–1088.
Dodt et al FEBS vol. 165 pp. 180–184 (1984).
Itakira et al Science vol. 209 pp. 1401–1405 (1980).

*Primary Examiner*—Vasu S. Jagannathan
*Assistant Examiner*—K. Cochrane Carlson
*Attorney, Agent, or Firm*—Burns, Doane, Swecker & Mathis, L.L.P.

[57] ABSTRACT

The present invention relates to variants of hirudin containing an amino acid different from the amino acid in the natural form at position 47 or 63.

7 Claims, 2 Drawing Sheets

FIG. 1

SEQUENCES OF 3 NATURAL VARIANTS OF HIRUDIN

|      | 1   | 2   | 3   | 4   | 5   | 6   | 7   | 8   | 9   | 10  | 11  | 12  | 13  | 14  | 15  |
|------|-----|-----|-----|-----|-----|-----|-----|-----|-----|-----|-----|-----|-----|-----|-----|
| 1HV1 | VAL | VAL | TYR | THR | ASP | CYS | THR | GLU | SER | GLY | GLN | ASN | LEU | CYS | LEU |
| 2HV2 | ILE | THR | TYR | THR | ASP | CYS | THR | GLU | SER | GLY | GLN | ASN | LEU | CYS | LEU |
| 3HV3 | ILE | THR | TYR | THR | ASP | CYS | THR | GLU | SER | GLY | GLN | ASN | LEU | CYS | LEU |

| 16  | 17  | 18  | 19  | 20  | 21  | 22  | 23  | 24  | 25  | 26  | 27  | 28  | 29  | 30  |
|-----|-----|-----|-----|-----|-----|-----|-----|-----|-----|-----|-----|-----|-----|-----|
| CYS | GLU | GLY | SER | ASN | VAL | CYS | GLY | CLN | GLY | ASN | LYS | CYS | ILE | LEU |
| CYS | GLU | GLY | SER | ASN | VAL | CYS | GLY | LYS | GLY | ASN | LYS | CYS | ILE | LEU |
| CYS | GLU | GLY | SER | ASN | VAL | CYS | GLY | LYS | GLY | ASN | LYS | CYS | ILE | LEU |

| 31  | 32  | 33  | 34  | 35  | 36  | 37  | 38  | 39  | 40  | 41  | 42  | 43  | 44  | 45  | 46  | 47  |
|-----|-----|-----|-----|-----|-----|-----|-----|-----|-----|-----|-----|-----|-----|-----|-----|-----|
| GLY | SER | ASP | GLY | CLU | LYS | ASN | GLN | CYS | VAL | THR | GLY | GLU | GLY | THR | PRO | LYS |
| GLY | SER | ASN | GLY | LYS | GLY | ASN | GLN | CYS | VAL | THR | GLY | GLU | GLY | THR | PRO | ASN |
| GLY | SER | CLN | GLY | LYS | ASP | ASN | GLN | CYS | VAL | THR | GLY | GLU | GLY | THR | PRO | LYS |

| 48  | 49  | 50  | 51  | 52  | 53  | 54  | 55  | 56  | 57  | 58  | 59  | 60  | 61  | 62  | 63  | 64  | 63  |
|-----|-----|-----|-----|-----|-----|-----|-----|-----|-----|-----|-----|-----|-----|-----|-----|-----|-----|
| PRO | GLN | SER | HIS | ASN | ASP | GLY | ASP | PHE | GLU | GLU | ILE | PRO | GLU | GLU | TYR | LEU | GLN |
| PRO | GLU | SER | HIS | ASN | ASN | GLY | ASP | PHE | GLU | GLU | ILE | PRO | GLU | GLU | TYR | LEU | GLN |
| PRO | GLH | SER | HIS | ASN | GLN | GLY | ASP | PHE | GLU | PRO | ILE | PRO | GLU | ASP | TYR | ASP | GLU |

↓ 64 65 66
ALA
63

1. From DODT et al. FEBS LETTERS 1984 <u>165</u>, 180-183.
2. From HARVEY et al. Proc. Natl. Acad. USA 1986 <u>83</u>, 1084-1088.
3. From DODT et al. Biol. Chem. Hoppe-Seyler 1986 <u>367</u>, 803-811.

5,650,301

HIRUDIN HV2 HAVING A SN7LYS SUBSTITUTION, METHOD OF MAKING, AND METHOD OF USE

This application is a continuation of application No. 08/197,449, filed Feb. 16, 1994, now abandoned, which was a continuation of Ser. No. 07/967,548 filed Oct. 27, 1992, now abandoned, which was a continuation of Ser. No. 07/627,876 filed Dec. 13, 1990, now abandoned, which was a continuation of Ser. No. 07/127,159 filed Dec. 1, 1987, now abandoned.

BACKGROUND OF THE INVENTION

At least 3 natural variants of hirudin are described in the literature (Markwardt 1970; Petersen et al. 1976; Markwardt and Walsmann 1976; Chang 1983; Dodt et al., 1984, 1985, 1986; Harvey et al. 1986; French Patent 84.04.755).

A comparison of the sequences of these 3 variants is shown in FIG. 1.

The first variant, HV1, corresponds to the hirudin which is isolated from the body of leeches; the second, HV2 (Harvey et al. 1986), differs from the first by 9 amino acids; the third (Dodt et al. 1986) is identical to HV2 as far as the serine 32, but differs by 10 amino acids in the C-terminal portion, which comprises, in addition, an additional amino acid (Ala63). This third variant will be designated hereinafter HV3.

These sequences contain 65 or 66 amino acids and may be regarded as 2 domains: a globular N-terminal portion, which contains 3 disulfide bridges, and an acidic C-terminal portion which possesses a homology with the site of cleavage by thrombin in the prothrombin molecule. This homology suggests that the region which surrounds position 47 might be the binding site of hirudin to thrombin.

Moreover, natural hirudin contains a sulfated tyrosine at position 63 (Chang, 1983). This sulfated tyrosine reappears at position 64 in the variant HV3. It will be designated hereinafter "position 63" for all the variants, its function being the same irrespective of its position.

A comparative analysis of the sequences of the natural variants of hirudin make it possible to envisage, theoretically, the creation of new variants in which the characteristics of the natural molecules are combined in different ways.

HV1 and HV3 have a lysine at position 47, situated between 2 prolines, which is probably responsible for blocking the active site of thrombin (Dodt et al. 1984 and 1985).

Since HV2 does not have a basic residue at this position but an asparagine, it seems desirable to substitute lysine or an arginine at this point in order to make the molecule more consistent with the features expected of a thrombin inhibitor (Chang 1985), or alternatively a histidine, which is not consistent with being a good substrate for thrombin but which might increase the inhibitory power of the hirudin.

Moreover, the sulfation of the tyrosine 63 represents a difference between natural hirudin and the hirudin obtained by genetic recombination which might have repercussions on its activity, as suggested by the kinetic studies of Stone and Hofsteenge (1986). An attempt may be made to mimic the native protein by replacing the tyrosine by an acidic residue such as Glu or Asp.

SUMMARY OF THE INVENTION

The present invention relates to variants of hirudin which contain an amino acid different from the amino acid existing in the natural form at position 47 or 63.

Such a variant is preferably a variant of hirudin HV1, HV2 or HV3.

Among the variants in question, the following should be mentioned:

the variants in which the amino acid $Tyr^{63}$ has been replaced by an acidic residue, especially Glu or Asp;

the variants in which the amino acid at position 47 in the natural form is replaced by an Arg or His;

the variants in which the $Asn^{47}$ of the natural form of HV2 is replaced by an Lys.

The following preferred variants should be mentioned in particular:

$[Lys^{47}]$ HV2

$[Arg^{47}]$ HV2

$[His^{47}]$ HV2

$[Glu^{63}]$ HV2

$[Asp^{63}]$ HV2

The variant, referred to above, of the present invention, namely $(Lys^{47})HV2$ [or "rHV2-Lys 47"], corresponds to the following formula:

ILE THR TYR THR ASP CYS THR GLU SER GLY GLN
ASN LEU CYS LEU CYS GLU GLY SER ASN VAL
CYS GLY LYS GLY ASN LYS CYS ILE LEU GLY
SER ASN GLY LYS GLY ASN GLN CYS VAL THR
GLY GLU GLY THR PRO LYS PRO GLU SER HIS
ASN ASN GLY ASP PHE GLU GLU ILE PRO GLU
GLU TYR LEU GLN

The different variants which have retained the $Tyr^{63}$ may be used in the sulfated form or otherwise. This sulfation may be produced chemically or biologically.

BRIEF DESCRIPTION OF THE DRAWINGS

FIG. 1 depicts an alignment of the three natural variants of hirudin, namely HV1, HV2, and HV3.

DESCRIPTION OF THE PREFERRED EMBODIMENTS

Figure 2:
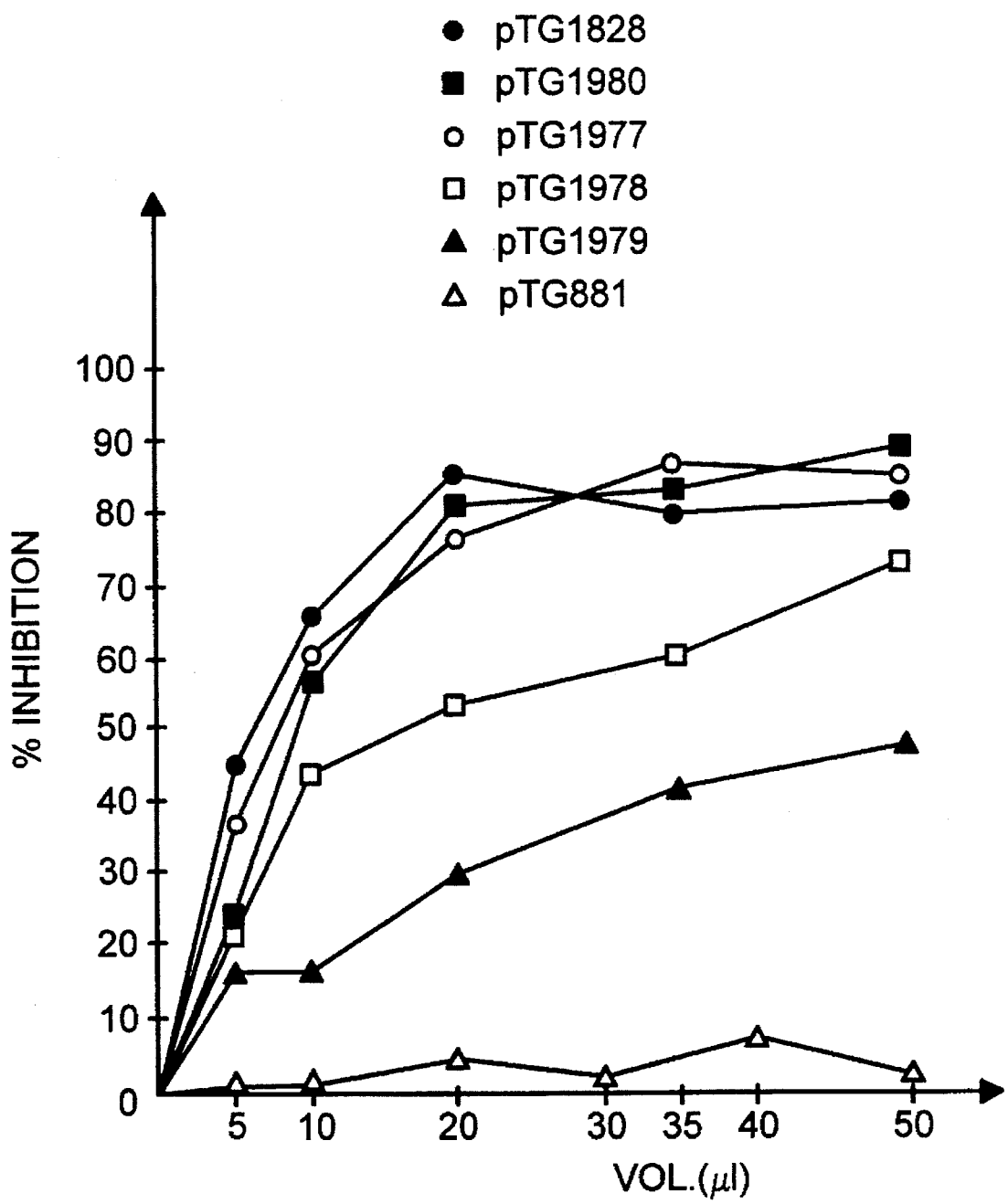
FIG. 2 depicts the percentage of inhibition of proteolytic activity of thrombin on chromozyme in terms of the volumes of supernatants of yeast cultures producing hirudin or HV2 or its variants.

The present invention encompasses the biological and/or chemical methods by means of which the abovementioned variants may be prepared.

These variants may, in effect, be obtained synthetically, semisynthetically and/or by the known techniques of genetic manipulation.

Thus, for example, the cloning and expression of the different sequences coding for HV1, HV2 and HV3, especially HV2, and the production of the corresponding hirudins from yeast cultures, have been described in Patent Application EP-A-200,655.

The variants according to the invention may be obtained by equivalent techniques after modifying the coding sequences mentioned above, for example by directed mutagenesis.

In particular, by in vitro directed mutagenesis, variants were constructed in which the asparagine 47 is replaced by a lysine, an arginine or a histidine, and in which the tyrosine 63 is replaced by a glutamic acid.

In particular, it is possible to use functional expression blocks as described in Patent Application EP-A-200,655, and in which the hirudin sequence codes for the above variants; these functional DNA blocks may be carried by a vector plasmid.

In order to direct the expression and secretion by yeast of the genes corresponding to the different variants, the latter are integrated in a vector for yeast which preferably comprises the following elements, which have been described in Patent Application EP-A-200,655:

the origin of replication of the 2μ plasmid of yeast, the ura3 gene, an origin of replication in E. coli and a marker for resistance to an antibiotic, a transcription promoter, the leader sequence and the prepro sequence of the precursor of the alpha factor, this sequence being fused in phase, upstream from the coding sequence for the variant of hirudin, the transcription terminator of the PGK gene of yeast, which will be placed downstream from the gene for the said variant.

The invention also relates to the yeasts transformed by these vectors or by this functional DNA block, and their application to the preparation of the variants of hirudin.

In particular, the invention relates to a method for preparing a variant of hirudin by fermentation of a yeast according to the invention, and recovery of the hirudin produced in the culture medium in mature form or in the form of a precursor which can be matured in vitro.

The techniques employed have already been described in greater detail in Patent Applications EP-A-200,655 and EP-87 401649.6.

The variants of hirudin thereby obtained may be used as described in Patent Application EP-A-200,655, as a thrombin inhibitor, both in vivo and in vitro.

In particular, these variants may be used in pharmaceutical compositions, alone or in combination with other active principles, or alternatively in the context of tests or of diagnosis, in vitro or in vivo. In the latter case, it may be advantageous to label the variants, for example by a radioactive, fluorescent, enzymatic or other labeling.

The present invention is illustrated by the examples which follow, with the aid of FIG. 1 which shows the sequences of 3 natural variants of hirudin, namely HV1, HV2 and HV3, and with the aid of FIG. 2 which shows the percentage inhibition of the proteolytic activity of thrombin on chromozyme in terms of the volumes of supernatants of yeast cultures producing hirudin or HV2 or its variants.

Example 1 Constructions of the different variants of HV2 by in vitro mutagenesis.

To perform an in vitro directed mutagenesis, the DNA fragment which it is desired to modify is cloned into the replicative form of a single-stranded phage; the genome of the recombinant phage is isolated and hybridized with a synthetic oligonucleotide which carries the mutated sequence. This oligonucleotide serves as a primer for the synthesis of the complementary strand and the DNA, thereby rendered double-stranded, is used for transforming a receptor bacterium which will produce the phage carrying the desired mutation (Zoller and Smith, 1983).

Plasmid pTG720, described in Patent EP-A-158,564, is a vector for the expression of hirudin in E. coli. Plasmid pTG730 was derived from pTG720 by the addition of an EcoRI site downstream from the coding sequence for hirudin. The EcoRI site enables the coding sequence for hirudin to be recovered by digestion with EcoRI on the one hand and ClaI on the other hand.

The ClaI-EcoRI fragment covers the entire coding region for hirudin less a few 5'-terminal codons. This ClaI-EcoRI fragment was cloned between the AccI and EcoRI sites of a derivative of phage M13, referred to as M13TG131 (Kieny et al., 1983). The phage derived from M13TG131, and which comprises this hirudin sequence, is designated M13TG1919.

Three oligonucleotides were synthesized, each of which is capable of pairing with the sequence 5'-GTACACCGAACCCTGAAAG-3' of M13TG1919, except for their central region which corresponds to the desired mutation. The sequences of these oligonucleotides are as follows:

TG435 5'-CTTTCAGGGTGCGGTGTAC-3'

TG436 5'-CTTTCAGGTTTCGGTGTAC-3'

TG437 5'-CTTTCAGGGCGCGGTGTAC-3'

These oligonucleotides were designed to enable the AAC (Asn) codon of M13TG1919 to be substituted by CAC (His) or AAA (Lys) or CGC (Arg), respectively.

120 picomoles of each oligonucleotide were phosphorylated in 100 μl of reaction medium, and approximately 20 picomoles of phosphorylated oligonucleotide were hybridized with 1 picomole of single-stranded DNA of phage M13TG1919 in 25 microliters of hybridization buffer.

After hybridization, the mixture of DNAs was subjected to the action of Klenow polymerase and to phage T4 ligase. Each mixture thus treated was used to transfect E. coli strain 71/18 (mut L) on lawns of indicator bacteria JM103 (Messing et al., 1981). The infected cells are identifiable because they form plaques which grow more slowly; the colonies were subcultured on complete medium and then transferred to Whatman 540 paper for the purpose of screening the cells possessing the mutated phages.

This screening is carried out by in situ hybridization with the oligonucleotide used above as a primer. Three new phages possessing the desired mutated sequence were thereby obtained:

M13TG1921 (Asn$^{47}$→Arg), M13TG1924 (Asn$^{47}$→His) and M13TG1925 (Asn$^{47}$→Lys).

Furthermore, the same type of experiment was carried out with an oligonucleotide TG434 having the sequence 5'-ATTGTAA<u>CTCTT</u>CTTCTG-3'. This oligonucleotide hybridizes with the sequence 5'-CAGAAGAA TATTTACAAT localized in the 3' region of the sequence coding for HV2, with an unpaired triplet designed to substitute the TAT (Tyr$^{63}$) codon by GAG (Glu). The corresponding mutated phage M13TG1922 (Tyr$^{63}$→Glu) was thereby obtained.

Example 2 Substitution of the (0.6-kb) PstI-HindIII fragment of pTG1828 by the mutated fragment.

Plasmid pTG1828 (described in Patent Application EP-87 401649.6) carries the coding sequence for hirudin, preceded by the prepro sequences of the gene for the alpha sex pheromone of yeast; the assembly is placed under the control of the PGK promoter. By means of this fusion between the prepro sequences of MF and hirudin, the expressed protein follows the normal yeast pathway of secretion and maturation, so that the processed and active hirudin appears in the culture medium.

This plasmid was employed again for expressing the sequences of mutated hirudin in place of the native hirudin.

The digestion of pTG1828 with PstI and HindIII releases five fragments having the approximate sizes 3.8, 1.9, 1.5, 1.1 and 0.6 kb, respectively. The last fragment comprises the preprohirudin fused sequence. This fragment comprises only a single AccI site and a single EcoRI site. The region bounded by these two sites comprises the entire hirudin sequence less a few 5'-terminal codons. The 0.6-kb HindIII-PstI fragment was inserted between the HindIII and PstI sites of a vector which possesses neither an EcoRI nor an AccI site.

The plasmid reconstituted in this manner (pTG1960) hence possesses a single AccI site and a single EcoRI site localized, respectively, at the beginning of the hirudin sequence and downstream from the latter. The digestion of pTG1960 with AccI and EcoRI releases a fragment which comprises virtually the entire hirudin sequence and the remainder of the plasmid.

The large DNA fragment from which the hirudin sequence has been deleted is purified on gel and mixed with the product of AccI/EcoRI digestion of the replicative form of each of the mutated phages described in Example 1, for the purpose of reconstituting the preprohirudin with the new HV2 variants obtained by directed mutagenesis. Four new plasmids were selected: pTG1963 (Asn$^{47}$→Arg), pTG1964 (Tyr$^{63}$→Glu), pTG1965 (Asn$^{47}$→His) and pTG1966 (Asn$^{47}$→Lys), which differ from pTG1960 only in respect of the mutated codons.

These sequences carrying the mutated codons may be recovered in the form of PstI-HindIII fragments and recloned in the vector pTG1828 in place of the original PstI-HindIII fragment.

4 new plasmids were thereby obtained: pTG1977 (Asn$^{47}$→Arg), pTG1978 (Tyr$^{63}$→GLu), pTG1979 (Asn$^{47}$→His) and pTG1980 (Asn$^{47}$→Lys), which differ from pTG1828 described above only in respect of the mutations created in vitro.

Example 3 Transformation of TGY1sp4 with the DNAs of pTG1977, pTG1978, pTG1979 and pTG1980.

S. cerevisiae TGY1sp4 (Mat α ura3.251.373.382 his-3.11.15) cells were transformed with the DNAs of pTG1977, pTG1978, pT61979 and pTG1980. ura$^+$ transformants were obtained in each case.

4 strains, TGY1sp4 pTG1977, TGY1sp4 pTG1978, TGY1sp4 pTG1979 and TGY1sp4 pTG1980, are hence obtained. The production of hirudin by these 4 strains and by TGY1sp4 pTG1828 was compared.

20 ml of culture (YNBG+0.5% casamino acids) at OD$_{660}$ 0.02 were seeded with each strain. After 48 h of agitation at 30° C. the cultures were centrifuged (5000 rpm, 5 min) and the supernatants assayed. A culture of TGY1sp4 pTG881 (plasmid not carrying the coding sequence for HV2) was used as a control.

The activity of the crude supernatants is measured in terms of their inhibitory effect with respect to thrombin activity (proteolytic activity on a synthetic substrate, chromozyme TH—Boehringer Mannheim). The percentage inhibition in terms of the volumes of supernatant is given in FIG. 2.

It is observed that the inhibitory effect produced by the Arg$^{47}$ and Lys$^{47}$ variants is at least equal to that of native HV2. The Glu$^{63}$ and His$^{47}$ variants are slightly less inhibitory than HV2.

Example 4 Inhibition of thrombin activity

In order to demonstrate more clearly the value of the variants of hirudin which are the subject of the invention, especially for the purpose of their pharmaceutical application, the comparative examples which follow illustrate the inhibitory properties with respect to thrombin of the variant HV2 and two other variants of the HV2 form, in which the amino acid at position 47 is replaced by an Arg or a Lys, all of which are obtained via recombinant DNA.

To study the kinetics of inhibition of thrombin by these variants, the theory of high affinity inhibitors, as described in J. W. WILLIAMS and J. F. MORRISON Methods in Enzymology 63 pp. 437–467, 1979, is used, since hirudin is a reversible inhibitor of thrombin.

The variants of hirudin used are purified to 95% and the Sigma pure human thrombin has a percentage activity, measured by titration of the active site, which is above 92%. The concentration of human thrombin is the same for all the measurements, namely 5.5×10$^{-9}$M. The medium is an 0.05M sodium PIPES buffer, pH 7.9, 0.18M KCl and 0.1% PEG at 37° C. The thrombin substrate is Boehringer chromozyme PL. A preincubation time of 2 minutes is observed for the thrombin and hirudin, and the reaction is then initiated with the substrate.

The following table summarizes the values determined experimentally for the quantity of hirudin required for a 95% inhibition of the same quantity of human thrombin (5.5×10$^{-9}$M).

|  | Quantity for attaining 95% inhibition of thrombin (10$^{-9}$ M) |
|---|---|
| HV2 Lys$^{47}$ | 7.6 |
| HV2 Arg$^{47}$ | 8.5 |
| HV2 | 32.2 |

It is hence seen that approximately 4-fold less hirudin HV2 Arg$^{47}$ and HV2 Lys$^{47}$ than hirudin HV2 is required for inhibiting the same quantity of human thrombin.

The proposed variants hence have inhibitory properties with respect to thrombin which are markedly improved.

Example 5 Preliminary pharmacological study of two variants of recombinant hirudin, rHV2 and rHV2-Lys 47, compared with standard heparin.

1—OBJECT OF THE STUDY

To assess two variants of recombinant hirudin, rHV2 (or HV2) and rHV2-Lys 47 [or (Lys$^{47}$)HV2], and compare their antithrombotic efficacy with standard heparin. Both of these variants are devoid of post-transcriptional sulfation of the Tyr 63 group.

2—EXPERIMENTAL CONDITIONS a) The specific antithrombin activity (human and bovine thrombin) of the two recombinant hirudins in physiological saline is determined on the basis of the inhibition of the proteolytic activity of thrombin on chromozyme.

b) The anticoagulant activity of the two hirudins is compared in vitro in rat and rabbit plasma in terms of prolongation of the thrombin time, and the anti-IIa effect is measured chromogenically.

c) The kinetics of disappearance of hirudin from the plasma after i.v. bolus injection are followed by measuring the anti-IIa effect, using the thrombin time and chromogenically by means of calibration curves.

d) The plasma concentrations obtained after 30 minutes' continuous i.v. perfusion in rabbits are determined by the same techniques.

e) The antithrombotic activity of the two variants of hirudin and of standard heparin is studied in Wessler's rabbit and rat model, with thromboplastin as thrombogenic agent, and in the model of stasis in rabbits (Fareed). The compounds are administered by continuous perfusion in rabbits and by i.v. bolus in rats.

The models used are as follows:

Wessler's model in rabbits

Male New Zealand rabbits weighing 2.5 to 3 kg were used in this study. After anesthesia by intravenous injection of pentobarbital sodium (30 mg/kg), the left carotid was cannulated and the two jugular veins were isolated; two slack ligatures were placed on each of them at a distance of 2.5 cm from one another. The rabbits then received either physiological saline or solutions of hirudin or heparin in continuous perfusion for 30 minutes at a flow rate of 2.5 ml/hour. Two minutes before the end of the perfusion, arterial blood samples were drawn in order to determine the plasma levels of the anti-coagulants. One minute before the end of the perfusion, human thromboplastin (Manchester Comparative Reagents Ltd), standardized according to M. Buchanan's procedure, was injected at a dose of 600 ug/kg during exactly 30 seconds into the aorta via the carotid. Thirty seconds later the perfusion was stopped and blood stasis was produced by tightening the ligatures on the two venous segments for 15 minutes. The jugulars were then opened and the thrombi extracted, rinsed in physiological saline and weighed after blotting with filter paper.

Wessler's model in rats

Male (CD-COBS) Sprague-Dawley rats weighing approximately 300 g were used. After anesthesia with pentobarbital sodium i.p. (30 mg/kg) and median laparotomy, the inferior vena cava was exposed over 1 cm measured from the renal intersection. Two flexible ligatures were positioned 0.7 cm apart.

The test products, diluted in physiological saline, were injected in an i.v. bolus at 1 ml/kg, 5 min 40 s or 1 min (heparin) before the production of venous stasis. Forty seconds before this stasis, a thrombogenic agent (rabbit thromboplastin, E. Dade) was injected at a dose of 25 mg/ml/kg into the vein of the penis in the space of 30 seconds, measured very exactly. Ten seconds after the end of the injection, stasis was established by tightening the two ligatures, first the proximal and then the distal. The stasis was maintained for 10 minutes, and the thrombus was then removed, immersed in a 0.38% strength citrate solution, dried with general-purpose absorbent paper and weighed on the following day after drying for one hour at 500° C.

Model of thrombosis by blood stasis in rabbits

Male New Zealand rabbits weighing 2.5 to 3 kg were used in this study. After intravenous anesthesia with pentobarbital sodium (30 mg/kg), the left carotid was cannulated and the two jugular veins were isolated; two slack ligatures were placed on each of them, at a distance of 2.5 cm from one another. The rabbits then received either physiological saline or solutions of hirudin or heparin in continuous perfusion for 30 minutes, at a flow rate of 2.5 ml/hour. Two minutes before the end of perfusion, arterial blood samples were drawn in order to determine the plasma levels of the anticoagulants. At the same time as the perfusion was stopped, stasis was established by tightening the four ligatures (first the proximal and then the distal). The stasis was maintained for 2 hours, the jugulars were then opened and the thrombi extracted, rinsed in physiological saline and weighed after blotting with filter paper.

3—RESULTS a) For a preparation of stock solution at a concentration of 1 mg/ml, the specific antithrombin activity of the two variants of hirudin with respect to human and bovine thrombins is expressed in Table 1 below:

TABLE 1

|  | r HV2 | rHV2-Lys 47 |
|---|---|---|
| for human thrombin | 14,800 | 19,000 |
| for bovine thrombin | 15,500 | 19,200 |
| (results expected for human thrombin) | (13,300) | (16,000) |

The specific antithrombin activity of the hirudin variant rHV2 is +/− 15,000 ATU/mg, and +/− 19,000 ATU/mg for the variant rHV2-Lys 47. These specific activities are greater than those expected. The specific activity is identical for the human and bovine thrombins.

b) The anticoagulant activity in rat and rabbit plasma, determined in terms of the thrombin time, is equivalent for low concentrations of the two hirudins. The variant rHV2-Lys 47 is markedly superior for higher concentrations. The amount of residual thrombin in the rat and rabbit plasma, determined by means of a chromogenic substrate, is comparable after adding the two hirudins up to 60 ATU/ml. For further neutralizing the traces of residual thrombin, the variant rHV2-Lys 47 is more effective. This reflects the difference in the Ki values.

c) the kinetics of disappearance of the two hirudins from the plasma after i.v. bolus injection is comparable for the chromogenic determination, but slightly different for the determination in terms of the thrombin time (Table 2). The hirudins disappear according to two exponentials. A first phase (distribution) with a t ½ α of approximately 3 min, which reduces the first initial quantity by 60% in the space of 5 min for both hirudins; and a second phase (elimination), with a t ½ β of 16 min for rHV2-Lys 47 and 28 min for rHV2 if the thrombin time is considered, and 28 and 30 min, respectively, if the chromogenic method is employed. The standard heparin disappears according to a single exponential phase (t ½=9 min).

TABLE 2

| Half-life in minutes of the hirudins after I.V. bolus injection in rabbits | | | | |
|---|---|---|---|---|
|  | t ½ α | | t ½ β | |
| Method | TT | CS | TT | CS |
| rHV2 | 2.5 | 3.0 | 28 | 28 |
| rHV2-Lys 47 | 1.8 | 3.0 | 16 | 30 |

TT: thrombin time
CS: chromogenic substrate d) The plasma concentration of the two variants of hirudin obtained after 30 minutes' continuous i.v. perfusion in rabits are in a linear relationship with the doses perfused.

e) Antithrombotic effects

| PRODUCTS | RABBIT i.v. perfusion ug/kg/h | | RAT i.v. bolus ug/kg WESSLER | |
|---|---|---|---|---|
| | WESSLER | STASIS | −5 min 40 s | −1 min |
| rHV2 | 375 | — | 240 | |
| rHV2-Lys 47 | 20 | 47 | 160 | |
| Standard heparin | 110 | 110 | 160 | 110 |

On the basis of these preliminary pharmacological results, it appears that, in continuous perfusion in rabbits, the variant of recombinant hirudin rHV2-Lys 47 has an antithrombotic activity which is superior to those of rHV2 and heparin. The pharmacokinetics of the two variants of hirudin are identical.

Example 6 Comparison of the ratio antithrombotic activity/risk of hemorrhage for hirudin rHV2-Lys 47 and standard heparin.

The studies carried out show that the risk of hemorrhage in rabbits and the prolongation of the bleeding time in rats, treated with rHV2-Lys 47, are less than those in animals treated with standard heparin, on the basis, for each species, of doses that have equal activity in a model of thrombosis.

Deposition of strains representing the invention

The following strains were deposited at the Collection Nationale de Cultures de Microorganismes (National Collection of Microorganism Cultures) of the Institut Pasteur, 28 Rue du Docteur Roux, Paris (15), on 6th November 1986:
TGY1sp4 pTG1977 (HV2-Arg$^{47}$) under No. I-621
TGY1sp4 pTG1980 (HV2-Lys$^{47}$) under No. I-622.
The reference strain had been deposited on 6th June 1986:
TGY1sp4 pTG1828 under No. I-569.

REFERENCES

Chang, J. Y. FEBS Letters X64, 307–313 (1983).
Chang, J. Y. Eur. J. Biochem. 15X, 217–224 (1985).
Dodt, J., Mueller, M. P., Seemüler, U & Chang, J. Y. FEBS Letters 165, 180–184 (1984).
Dodt, J., Seemüller, U., Maschler, R. & Fritz, H. Biol. Chem. Hoppe-Seyler 366, 379–385 (1985).
Dodt, J., Machleidt, W., Seemüler, U., Maschler, R. & Fritz, H. Biol. Chem. Hoppe-Seyler 367, 803–811 (1986).
Harvey, R. P., Degryse, E., Stefani, L., SChamber, F., Cazenave, J. P., Courtney, M., Tolstoshev, P. & Lecocq, J. P. Proc. Natl. Acad. Sci. USA 83, 1084–1088 (1986).
Kieny, M. P., Lathe, R. & Lecocq, J. P. Gene 26, 91–99 (1983).
Krajewski, T. & Blombäck, B. Acta Chemica Scandinavica 22, 1339–1346 (1968).
Markwardt, F. Methods Enzymol. 19, 924–932 (1970).
Messing, J., Crea, R., Seeburg, P. H. Nucl. Ac. Res. 9, 309 (1981).
Petersen, T. E., Roberts, H. R., Sottrup-Jensen, L. & Magnusson, S. Protides, Biol., Fluids, Proc. Colloq. 23, 145–149 (1976).
Stone, S. R. & Hofsteenge, J. Biochem. 25, 4622–4628 (1986).
Zoller, M. J. & Smith M. N. Methods in Enzymol. 100, 469 (1983).

We claim:

1. A HV2 (Lys47) variant of hirudin, consisting of the amino acid sequence: ILE THR TYR THR ASP CYS THR GLU SER GLY GLN ASN LEU CYS LEU CYS GLU GLY SER ASN VAL CYS GLY LYS GLY ASN LYS CYS ILE LEU GLY SER ASN GLY LYS GLY ASN GLN CYS VAL THR GLY GLU GLY THR PRO LYS PRO GLU SER HIS ASN ASN GLY ASP PHE GLU GLU ILE PRO GLU GLU TYR LEU GLN.

2. The HV2 (Lys 47) hirudin variant according to claim 1, wherein Tyr$^{63}$ is unsulfated.

3. The hirudin HV2 (Lys47) variant of claim 1, wherein Tyr$^{63}$ is sulfated.

4. A pharmaceutical composition suitable for injection comprising the hirudin variant according to claim 1.

5. A method for producing the hirudin HV2 (Lys47) variant of claim 1 comprising the following steps:

culturing a yeast cell which is transformed with a heterologous DNA fragment encoding said variant and which is capable of expressing said DNA fragment; and recovering said variant from the culture.

6. The method of claim 5, which comprises the steps of:

i. growing a culture of yeast fermentation, said yeast having been previously transformed either with a plasmid containing:

the origin of replication of the 2 u plasmid of yeast,
the ura3 gene,
an origin of replication in *Escherichia coli* and a marker for resistance to an antibiotic,
a transcription promoter, the "leader" sequence and the prepro sequence of the precursor of the alpha factor, this sequence being fused in phase, upstream from the coding sequence of the variant of hirudin,
the transcription terminator of the PGK gene of yeast, which will be placed downstream from the gene for the said variant, or with a DNA segment coding for said variant, under conditions such that said variant is produced in said culture; and ii. isolating said variant from said culture.

7. A method for preventing coagulation of blood in a mammal comprising the administration to said mammal of an anticoagulating effective amount of the pharmaceutical composition of claim 4.

* * * * *

UNITED STATES PATENT AND TRADEMARK OFFICE
CERTIFICATE OF CORRECTION

PATENT NO. : 5,650,301

DATED : July 22, 1997

INVENTOR(S) : Michael COURTNEY et al

It is certified that error appears in the above-indentified patent and that said Letters Patent is hereby corrected as shown below:

On the title page, item [54] and column 1.:

In the title, please change "A SN7LYS" to -- ASN47LYS --.

Signed and Sealed this

Twenty-seventh Day of July, 1999

Attest:

Q. TODD DICKINSON

*Attesting Officer*     *Acting Commissioner of Patents and Trademarks*